United States Patent
Moberly (10) Patent No.: US 9,497,423 B2
(45) Date of Patent: Nov. 15, 2016

(54) USB-ENABLED AUDIO-VIDEO SWITCH

(75) Inventor: David S. Moberly, Palo Alto, CA (US)

(73) Assignee: Koninklijke Philips N.V., Eindhoven (NL)

( * ) Notice: Subject to any disclaimer, the term of this patent is extended or adjusted under 35 U.S.C. 154(b) by 1857 days.

(21) Appl. No.: 12/278,342

(22) PCT Filed: Jan. 17, 2007

(86) PCT No.: PCT/US2007/060620
§ 371 (c)(1),
(2), (4) Date: Aug. 5, 2008

(87) PCT Pub. No.: WO2007/092660
PCT Pub. Date: Aug. 16, 2007

(65) Prior Publication Data
US 2009/0051765 A1    Feb. 26, 2009

Related U.S. Application Data

(60) Provisional application No. 60/765,628, filed on Feb. 6, 2006.

(51) Int. Cl.
*H04N 7/18* (2006.01)
*G06F 19/00* (2011.01)
(52) U.S. Cl.
CPC .......... *H04N 7/181* (2013.01); *G06F 19/3418* (2013.01)
(58) Field of Classification Search
CPC ............ H04N 7/17318; H04N 21/4622; H04N 21/4882; H04N 7/181; H04N
(Continued)

(56) References Cited

U.S. PATENT DOCUMENTS 5,553,609 A    9/1996   Chen et al.
5,724,968 A *  3/1998   Iliff .............................. 600/300
(Continued)

FOREIGN PATENT DOCUMENTS

EP    1126715 A2    8/2001
EP    1343326 A1    9/2003
(Continued)

OTHER PUBLICATIONS

By George Schreyer, "USB Charging Issues", Last Updated Jun. 11, 2005, http://www.girr.org/mac_stuff/usb_stuff.html, retrieved via archive.org.*

(Continued)

*Primary Examiner* — Christopher Biagini (57) ABSTRACT

A telemedicine system (8) includes an audio-video switch (10) that receives at least two different signals and conveys at least one of the at least two different signals to an output device (18) that presents it to a user. A control device (162) monitors a position of the audio-video switch (10) and automatically controls the position to select which of the at least two different signals is passed through the audio-video switch (10) to the output device (18) in response to a signal from a remote source (34). Signals received from the remote source (34) include medically related audio video message signals, which are input to the audio-video switch (10), and a control signal that causes the audio-video switch (10) to select between passing the medically related audio-video message signals and other received signals to the output device (18).

21 Claims, 3 Drawing Sheets

(58) Field of Classification Search
CPC .............. 21/42204;H04N 21/4316; G06F 19/3418
USPC .......................................................... 348/77
See application file for complete search history.

(56) References Cited

U.S. PATENT DOCUMENTS

| | | | |
|---|---|---|---|
| 5,808,659 A * | 9/1998 | Coutinho et al. ............. | 725/141 |
| 5,813,007 A * | 9/1998 | Nielsen ......................... | 709/206 |
| 6,177,931 B1 * | 1/2001 | Alexander ......... | G06Q 30/0269 348/565 |
| 6,717,609 B2 | 4/2004 | Sugimoto et al. | |
| 6,804,727 B1 * | 10/2004 | Rademacher .................... | 710/9 |
| 7,835,926 B1 * | 11/2010 | Naidoo et al. .................... | 705/3 |
| 2002/0054159 A1 * | 5/2002 | Obradovich ................... | 345/839 |
| 2002/0087643 A1 * | 7/2002 | Parsons et al. ............. | 709/206 |
| 2003/0070182 A1 * | 4/2003 | Pierre et al. .................. | 725/135 |
| 2003/0193577 A1 | 10/2003 | Doring et al. | |
| 2004/0010808 A1 * | 1/2004 | deCarmo ........................ | 725/139 |
| 2004/0268121 A1 * | 12/2004 | Shelest et al. ................ | 713/156 |
| 2005/0052527 A1 | 3/2005 | Remy et al. | |
| 2005/0134746 A1 * | 6/2005 | Brandt .......................... | 348/705 |
| 2006/0064476 A1 * | 3/2006 | Decasper et al. ............. | 709/223 |
| 2007/0137988 A1 * | 6/2007 | Yu et al. ........................ | 200/4 |
| 2009/0125475 A1 * | 5/2009 | Rhoads et al. ................. | 706/60 |

FOREIGN PATENT DOCUMENTS

| | | |
|---|---|---|
| JP | 9149386 A | 6/1997 |
| JP | 11267107 A | 10/1999 |
| JP | 2002259570 A | 9/2002 |
| JP | 2004166057 A | 6/2004 |

OTHER PUBLICATIONS uvswitch_README http://svn.navi.cx/misc/trunk/wasabi/devices/uvswitch/README; Jul. 24, 2008.
uvswitch_ERRATA http://svn.navi.cx/misc/truni/wasabi/devices/uvswitch/hardware/rev_a/ERRATA; Jul. 24, 2008.
uvswitch_image http://zero.navi.cx/gallery/uvswitach/im0009400; Jun. 9, 2005.
Key Digital Systems KD-SW4x1 (control via RS232 and IR remote control) http://www.ramelectronics.net/html/kd-sw4x1.htm; Jun. 9, 2005.
NTI VEEMUX-via Cat5 (control via CAT5E) http://www.42u.com/nti-matrix-video-switch-cat5.htm; Jun. 9, 2005.
uvswitch_schematic http://svn.navi.cx/misc/trunk/wasabi/devices/uvswitch/hardware/rev_a/schematic.pdf; Oct. 9, 2003.
uvswitch_pcb http://svn.navi.cx/nic/trunk/wasabi/devices/uvsiwtch/hardware/rev_a/pcb.pdf; 2003.

* cited by examiner

USB-ENABLED AUDIO-VIDEO SWITCH

DESCRIPTION

The following relates to electrical signal switching devices. It finds particular application to audio-video signal switching devices. More particularly, it is directed towards a controllable audio-video switch preferably via a Universal Serial Bus (USB) connection. However, other types of connections are also contemplated.

Conventional telemedicine includes the use of modern telecommunication and information technologies for the provision of clinical care to individuals located at a distance (e.g., at home, a nursing home, a retirement community, etc.) and to the transmission of information (e.g., messages, instructions, reminders, etc.) to provide that care. An exemplary telemedicine interaction may involve a store-and-forward form of telemedicine, a live form of telemedicine, and/or other forms of telemedicine. Store-and-forward telemedicine involves acquiring programming, data, images, video and/or audio and transmitting this information to an individual (e.g., a patient or medical specialist); it does not require the presence of the communicating parties at the same time and the bandwidth of the connection need not be high since latency is not an issue. Live telemedicine can be through television (e.g., via cable, satellite, etc.), computer (e.g., via dial-up, DSL (Digital Subscriber Line), cable modem, satellite, ISDN (Integrated Services Digital Network)), telephone, mobile telephone, etc. The live form of telemedicine typically requires the presence of the communicating parties at the same time and a high-bandwidth, low-latency connection for audio and/or video signals as well as tactile support.

One such telemedicine system is the Motiva™ telemedicine system. This system is primarily used by the elderly (however, it is not limited thereto), many of whom have limited ability in the field of interconnecting audio and/or video devices. In addition, physicians and/or other health care providers cannot be certain, with conventional telemedicine systems, whether audio and/or video information is reaching patients in a timely manner. In view of the above, there is an unresolved need for improved techniques for the delivery audio and/or video information within a telemedicine system.

In one aspect, a telemedicine system is illustrated. The telemedicine system includes an audio-video switch that receives at least two different signals and conveys at least one of the at least two different signals to an output device that presents it to a user. A control device monitors a position of the audio-video switch automatically controls the position to select which of the at least two different signals is passed through the audio-video switch to the output device in response to a signal from a remote source. The signals received from the remote source include medically related audio video message signals, which are input to the audio-video switch, and a control signal which causes the audio-video switch to select between passing the medically related audio-video message signals and other received signals to the output device.

One advantage includes automatic switching of an audio-video switch to display messages to a user.

Another advantage resides in external control of the audio-video switch.

Another advantage resides in a simplified interconnection of the audio-video switch with power, display, and other electronic devices.

Still further advantages will become apparent to those of ordinary skill in the art upon reading and understanding the detailed description of the preferred embodiments.

The drawings are only for purposes of illustrating embodiments and are not to be construed as limiting the claims.

Figure 1:
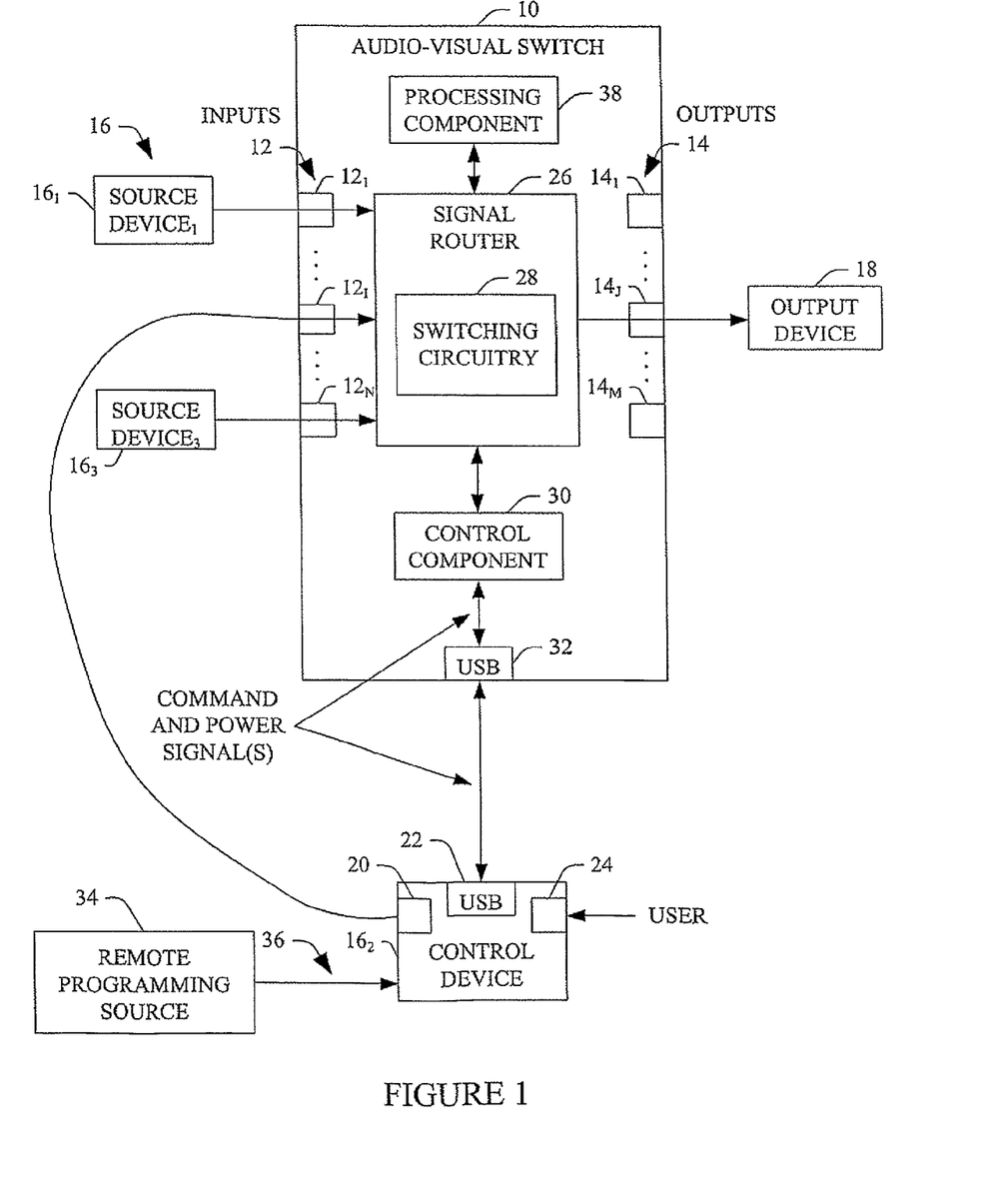
FIG. 1 illustrates an exemplary audio-video switch.

FIG. 1 illustrates a system 8 having an exemplary audio-video (AV) switch 10. The AV switch 10 includes N inputs $12_I, \ldots, 12_J, \ldots, 12_N$ (collectively referred to herein as inputs 12) and M outputs $14_I, \ldots, 14_J, \ldots, 14_M$ (collectively referred to herein as outputs 14), wherein I, N, J, and M are integers. Each of the inputs 12 is associated with one of composite video, s-video, RGB, component video or the like and includes corresponding connectors (e.g., BNC, RCA, s-video, wireless, etc.), which provide interfaces to one or more of suitable source devices 16. Each of the outputs 14 is also associated with one of composite video, s-video, RGB, component video or the like and includes corresponding connectors (e.g., BNC, RCA, s-video, wireless, etc.), which provide interfaces for a suitable output device 18.

Three source devices $16_1$, $16_2$, and $16_3$ are illustrated; however, in other instances, more (e.g., up to N) or less source devices 16 may be connected to the AV switch 10. Examples of suitable source devices 16 include, but are not limited to, a Motiva™ or other telemedicine receiver, a cable television receiver, a satellite receiver, a DVD player, a VCR player, a CD player, a computer, a digital camera, a digital video recorder, a control device, and the like. The output device 18 is connected to the AV switch 10 via the output $14_J$. However, in other instances the output device 18 can be connected to one of the other outputs 14 of the AV switch 10. The particular output 14 used depends on the type of connection (e.g., composite video, s-video, RGB, component video, etc.). Suitable output devices 18 include, but are not limited to, a television, a computer, a cell phone, a personal data assistant (PDA), a stereo system, a radio, and the like.

In this example, the source device $16_2$ is a control device such as a telemedicine receiver, a computer, a cable box, etc. The control device $16_2$ receives video and/or audio signals (e.g., messages, programs, warnings, instructions, movies, etc.) from a remote source via cable, satellite, phone line, RE signals or the like and with a transmitter 20 transmits the signals to the input $12_1$ of the AV switch 10. Control and/or power signals are also to the AV switch 10, for example, through a communications port such as a USB port 22 or the like, as described in detail below. The video and/or audio signals may be routed through the AV switch 10 and presented to the user via the output device 18. In some instances, only video is provided (e.g., textual messages). In other instances, only audio is provided (e.g., vocal recordings). In still other instances, a combination of video and audio (audio/video) are provided (e.g., a video recording with supporting sound). Typical audio and/or video input might include an instructional or motivational video for dealing with a medical condition, a reminder to take medications, a request to monitor physiological conditions, etc.

The control signal may include a command that controls which input signal(s) received at the inputs 12 passes through the AV switch 10 to the output device 18. The power signal powers the AV switch 10. A user can communicate with the control device 16$_2$ through a communication interface 24, which can include a TV remote, an alpha-numeric panel, a touch-screen display, a roller ball, a mouse, a digital pen, a microphone, various sensors (e.g., RF, IR, optical, etc.), and/or other input devices. Optionally, user communications signals can be received by the AV switch 10 and communicated to the control device, e.g., via the USB port. The other source devices 16$_1$ and 16$_3$ provide video and/or audio signals to the AV switch 10 via the inputs 12$_1$ and 12$_N$, respectively.

The signals received by the AV switch 10 (from the control device 16$_2$, the source device 16$_1$, the source device 16$_N$, etc.) are conveyed to a signal router 26 through various mediums (e.g., wire, conductive traces, wirelessly, optically, etc.). The signal router 26 includes video and audio switching circuitry 28 that selectively passes one or more of the received video and/or audio signals to the output device 18 based on a control command from a user or the control device 16$_2$.

A control component 30 controls the signal router 26. In one instance, the control device 16$_2$ sends control commands to the AV switch 10 that control the control component 30. As depicted, the control device 16$_2$ can communicate (uni or bi-directionally) with the control component 30 through a Universal Serial Bus (USB) port. For example, the USB port 22 of the control device 16$_2$ can be connected to a USB port 32 of the AV switch 10 through suitable media (e.g., a USS cable, wirelessly, etc.). In other instances, other ports such as serial, parallel, infrared, optical, radio frequency, etc. are additionally or alternatively used for (uni or bi-directional) communication. Through the port 22, the control device 16$_2$ can monitor the position of the AV switch 10, take over control of the AV switch 10, and automatically control it to ensure video and/or audio from the control device 16$_2$ is provided to the output device 18 for presentation to the user.

Alternately, the AV switch 10 can be controlled to provide programming from a different input. For example, received programming or other audio/video signals can be stored in a (local or remote) recorder source device and played back when the output device 18 is turned on, at a selected time, on-demand, or the like. Recording and later playback facilitates converting low bandwidth signals from the remote source 34 into high quality displays or other outputs and/or reducing signal size (e.g., via compression) prior to storing and/or playing a recorded audio-video signal. In addition, the control device 16$_2$ can also use the USB port 20 (and/or various other ports) to read information (e.g., a unique ID, a serial number, a software/firmware version, error logs, etc.) from the AV switch, write information (e.g., software/firmware updates, applications, etc.) to the AV switch 10, and execute routines (e.g., diagnostics, etc.) within the AV switch 10.

The control commands sent by the control device 16$_2$ may originate with a health care provider/facility or other remote programming source 34 transmitting information to the control device 16$_2$ (e.g., via cable, satellite, a LAN line 36, etc.). In one instance, the information transmitted to the control device 16$_2$ includes the control command. For example, the control device 16$_2$ may receive a control command that invokes the signal router 26 to pass the data (audio and/or video information) received at the input connected to the control device 16$_2$ through the AV switch 10 to the output device 18 through the output 14$_f$. In another example, the control device 16$_2$ may receive a control command that invokes the signal router 26 to pass audio and/or video (e.g., an instructional video) received from a different one of the source devices 12 (e.g., a community health channel provided through a cable box) to the output device 18.

In another instance, the information transmitted to the control device 16$_2$ by the source 34 or other source includes one or more messages. Examples of suitable messages include, but are not limited to, at least one of instructional programming relating to a disease or physiological condition, reminders to take medicines, reminders of medical appointments, requests to monitor physiological conditions, motivational programming, requests to call a doctor's office, instructions associated with a scheduled medical procedure, test results, and real-time communications from medical personnel. Reception of such message may invoke the control device 16$_2$ to send the control command (over the USB connection) to the AV switch 10 to control the signal router 26 accordingly. In addition, the received message(s) is sent to the AV switch by the control device 16$_2$ and routed through the signal router 26 to the output device 18.

The control command may also originate from the user. For example, the user may manually enter a command at the control device 16$_2$ through an interface 24. In another example, the user may use a remote control to send control commands to the control device 16$_2$ via the interface 24. This enables the user to select among source devices, play or replay the information from the remote source, and the like.

In one instance, a security mechanism is provided in which a party (e.g., the user, a health care provider, a third party such as family, etc.) attempting to communicate with (e.g., control, convey audio-video to, convey messages to, etc.) the control device 16$_2$ and/or the AV switch 10 is validated prior to allowing such communication. For instance, the control device 16$_2$ and/or the AV switch 10 may be programmed to only accept signals from a predetermined set of authorized health care facilities and/or individuals and/or other entities. A particular party desiring to communicate with (e.g., control, etc.) the control device 16$_2$ and/or the AV switch 10 may first have to provide identification indicia, an authorization code, a password, and the like that is validated by the control device 16$_2$ and/or the AV switch 10 before any such communication is allowed. Such validation could include comparing the received identification indicia, authorization code, password, etc. with stored authorized identification indicia, authorization code, password, etc.

The party may attempt to communicate with the control device 16$_2$ and/or the AV switch 10 through local controls (e.g., knobs, buttons, touch screen, etc. residing on the control device 16$_2$ and/or the AV switch 10), a remote control (e.g., a universal wireless remote programmed to communicate with the control device 16$_2$ and/or the AV switch 10), voice activated controls (e.g., executing voice recognition software in connection with a microphone), the Internet, the source 34, etc. In one instance, communication from an unauthorized party is ignored In this instance, information about the unauthorized party (e.g., obtained from the attempted communication) may be stored and/or sent to security and/or administrative authority for analysis. The predetermined set of authorized entities and information used for validation may be updated by an authorized entity such as the user adding a party (e.g., via a control panel, a wireless remote, voice controls, etc.), an authorized health care facility/provider writing to or overwriting (e.g., via downloading) previously stored authorization information via the source 34, etc.

Each received message may be associated with tag that indicates a priority of the corresponding message. In this instance, the control device $16_2$ can ascertain the relative importance of the message via the tag to determine whether the message should be presented to the user via the output device 18 or a notification (e.g., via the output device 18 or other visual and/or audio components) that a message has arrived, or whether the message should be stored for later retrieval without currently interrupting the user. Messages provided by health care providers/facilities can be associated with a relatively high priority in order to allow the control device $16_2$ to take control over the AV switch 10, overriding the user's source selection, and set the switch to display incoming messages from the control device $16_2$ to the user at the output device 18.

As briefly stated above, one or more audio and/or video signals received by the inputs 12 can be provided to the output device 18. For instance, the control component 30 can control the signal router 26 such that an audio and/or video signal conveyed from only one of the inputs 12 is passed through the AV switch 10 to the display device 18. In this instance, the user may initially select the audio and/or video signal that passes to the output device 18. However, when the control device $16_2$ transmits information to the AV switch 10, the control device $16_2$ may also issue a control command to the control component 30, instructing the control component 30 to switch the AV switch 10 such that the audio and/or video signals provided by the control device $16_2$ are fed to the output device 18. The control component 30 can switch the AV switch 10 back to the audio and/or video signal selected by the user after the user views/listens to the message. In one instance, the control device $16_2$ releases control of the AV switch 10 back to the control component 30 after a predetermined lapse of time, upon receiving an acknowledgement (e.g., electronic, audible, tactile, etc.) from the user that the message has been received, etc.

In another instance, video and/or audio messages from the control device $16_2$ can be concurrently presented with video and/or audio from at least one other source device 16. A processing component 38 is used to combine the signals. For example, a video message from the control device $16_2$ may be superimposed as an overlay, a banner, a semi-transparent image (with a programmable and adjustable translucence), or the like over the video from one of the other source devices 16 by the processing component 38, and the superimposed video may be provided to the output device 18. The audio, if any, associated with the video from the control device $16_2$ may override the audio associated with the video from the other source device 16. In this manner, the video and/or audio message from the control device $16_2$ can be presented to the user along with another video signal. In other instances, the processing component 38 is not used to combine signals and the video and/or audio messages from the control device $16_2$ are provided to the output device 18 instead video and/or audio from one of the other source devices 16.

The different messages transmitted by the control device $16_2$ may be associated with a similar or different priority levels such that some messages (e.g., an urgent announcement, etc.) are associated with relatively high priority levels that secure a transmission path dedicated for displaying messages at the output device 18, some messages (e.g., a general announcement, etc.) are associated with lower priority levels in which superimposed signals are conveyed to the output device is, and some messages are associated with relatively low priority levels in which the user is prompted as to whether the message should be displayed now or stored for later retrieval.

In another instance, one of the source devices 16 is a digital video recorder (DVR), a personal video recorder (PVR), or other device that allows a user to capture television or other video to a storage device for later viewing, or the like. When the user turns on the TV to watch a selected program, the control device causes a message recorded while the TV was off to be played while the selected program is recorded. After the message, the selected program is played back. As briefly discussed above, the control device $16_2$ may also provide power signals to the AV switch 10 through the USB connection between the USB port 22 and the USB port 32. The power signals may be used to power at least a portion of the AV switch 10. In another instance, the AV switch is additionally or alternatively powered by a power supply (e.g., an AC to DC converter plugged into a wall mounted AV receptacle), a battery, a photocell, or the like. The control device $16_2$ may also control power to the output device to turn the output device on, e.g., when a time-sensitive message is received.

Figure 2:
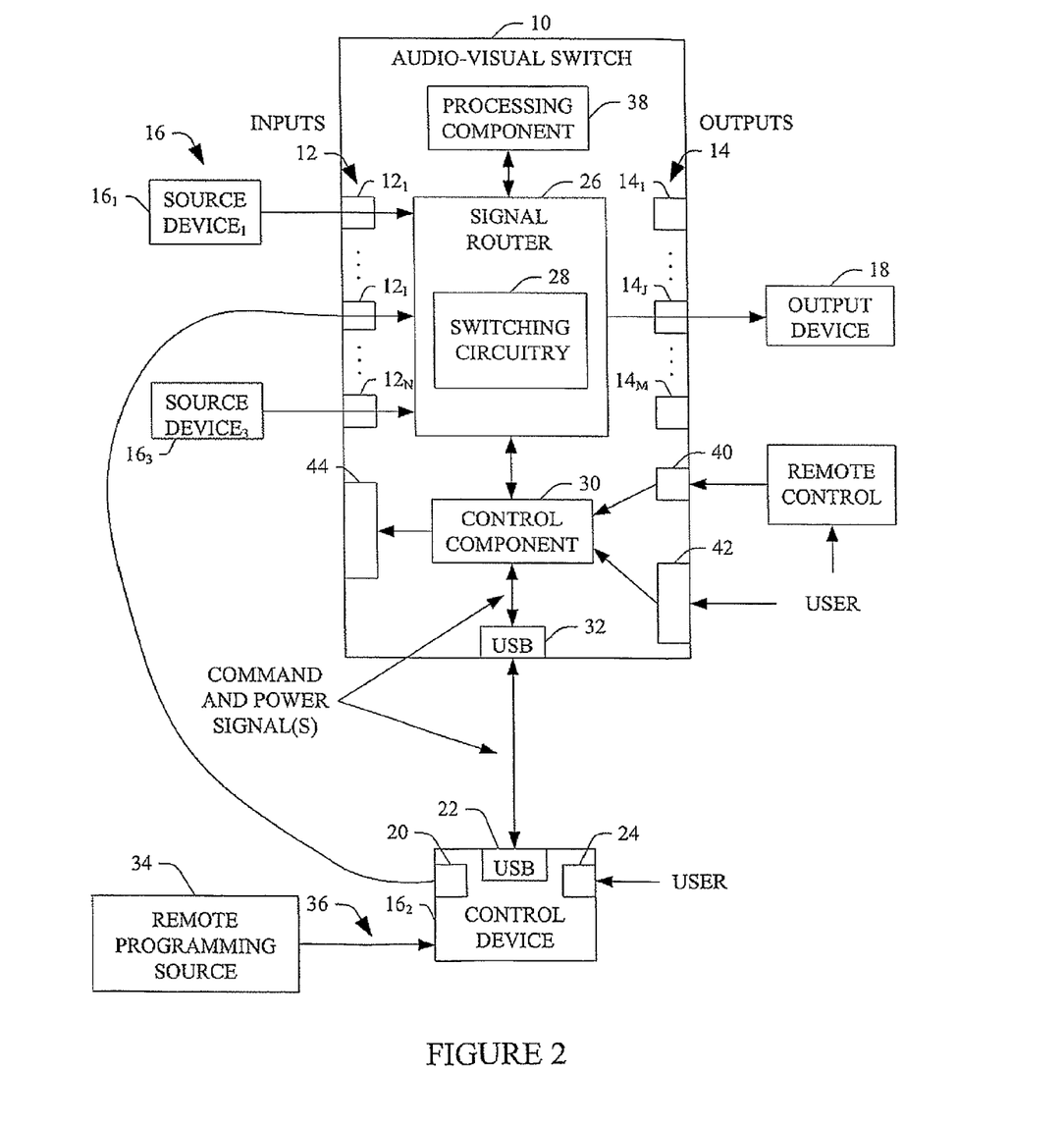
FIG. 2 illustrates an embodiment in which the AV switch includes input and output mechanisms that facilitate controlling the signal(s) that is passed to an output device.

FIG. 2 illustrates an embodiment of the system 8 in which the AV switch 10 further includes input and output mechanisms that facilitate controlling the signal(s) passed through the AV switch 10 and monitoring the status of the AV switch 10. In FIG. 2, common components with FIG. 1 are denoted with the same reference number.

As depicted, the AV switch 10 can include a wireless communications port 40. A user of the AV switch 10 can provide control commands to the control component 30 through this port. The control component 30 interprets such commands and controls the signal router 26 accordingly. For example, the user may use a remote control or other wireless transmitter that is programmed to communicate with the port 40 of the AV switch 10. The user can use the remote control to send various control commands such as a command that changes the input 12 that is fed to the output $14_j$ connected to the output device 18. The communications port 40 and the remote control can include various communication technologies such as radio frequency (RF), infrared (IR), optical, etc. for communication.

The AV 10 may additionally or alternatively include a control panel 42 with which the user can manually communicate with the AV switch 10. For instance, the user can enter a control command through the control panel 42 to select the input 12 whose signal will pass through the AV switch 10. The control panel 42 may be associated with various input/output mechanisms such as an alpha-numeric panel, a touchscreen, a mouse, a roller ball, a touch pad, a digital pen, a microphone to receive audible instructions, various sensors (e.g., RF, IR, optical, pressure, etc.), and/or other input devices.

The AV 10 may additionally or alternatively include a presentation component 44, which provides visual and/or audible feedback. For example, the presentation component 44 can include a plurality of light emitting diodes (LEDs) and/or seven segment displays that indicate one or more of whether the AV switch 10 is receiving power, the type of power (e.g., converted AC, battery or photocell), whether data is being received at each of the inputs 12, whether data is being conveyed through each of the outputs 14, error codes, whether the AV switch 10 is being controlled by the control device $16_2$, whether a message is being broadcast through the output device 18, etc. The presentation component 44 can additionally or alternatively include a flat panel display, a liquid crystal display (LCD), and the like to provide graphical and textual information, a speaker to provide audible information, etc.

Figure 3:
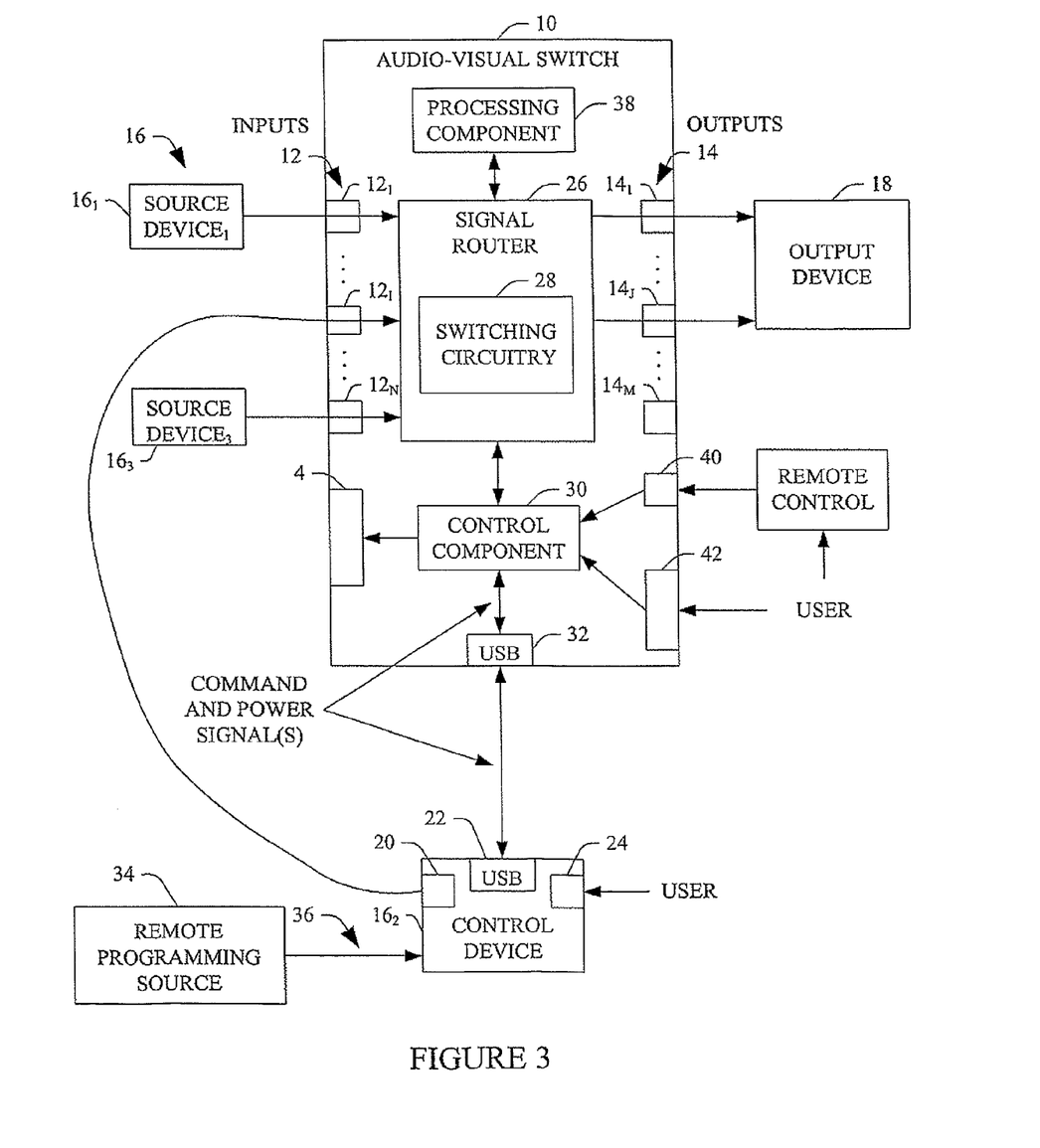
FIG. 3 illustrates an embodiment in which video and/or audio signals received by two or more inputs are provided to the output device.

FIG. 3 illustrates an embodiment of the system 8 in which video and/or audio signals received by two or more of the inputs 12 and passed to two or more of the outputs 14 are provided to the output device 18. For explanatory purposes, the inputs $12_1$, $12_1$ and $12_N$ are illustrated as receiving audio and/or video signals. The output device 18 may include picture-in-picture or similar technology in which the display area of the output device 18 can be delineated into two or more independent regions, each that can present different video. For explanatory purposes, only two of the outputs $14_1$ and $14_J$ provide similar or different video and/or audio signals to the output device 18.

The control component 30 can control the signal router 26 to pass one audio and/or video signal to one of the outputs 14, a different audio and/or video signal to a different one of the outputs 14, etc. Typically, one of the viewing regions of the output device 18 is designated as a primary region and audio associated with this region is provided to the user. The other region(s) are deemed secondary and typically present video without the audio. With conventional picture-in-picture technology, the user can change which region is the current primary region. Some systems allow the user to select the audio output such that audio from a secondary viewing region is broadcast. Both of these changes can be achieved via the AV switch 10 through the communications interfaces 40 and/or 42.

The control device $16_2$ can also change which audio and/or video signal is conveyed to the primary region and which audio and/or video signals are conveyed to the other regions of the output device 18. In one instance, the change is initiated by the reception of a message, which is subsequently provided to the user, by the control device $16_2$. For instance, a health care provider/facility may send a message to the user that informs the user that it is time to take a medication. Upon receiving such message, the control device $16_2$ may provide the message (e.g., which may include audio and/or video) to the input $12_1$ of the AV switch 10. Concurrently, another source device 16 may be providing audio and/or video to another of the inputs 12. The control device $16_2$ may send a control command to the AV switch 10 via the USB connection between the USB port 22 and the USB port 32. The control command is conveyed to the control component 30, which controls the signal router 26 to pass the message to the output 14 that feeds either the primary region or one of the secondary regions of the output device 18. The other audio and/or video signal can be displayed in another viewing region.

In instances where the message is deemed critical, the message may be sent to the output 14 feeding the primary region and the picture-in-picture feature can be either disabled or the signal feeding the display regions can be temporarily terminated, or the message may be sent to the outputs feeding the primary and the secondary regions of the output device 18 such that all display regions present the message. In instances where the message is deemed less important, the message may be sent to the output 14 feeding the primary region or an output 14 feeding a secondary region of the output device 18. For example, the selected programming can be switched to the secondary region which the message is displayed in the primary region. After the message is displayed, or, if the message calls for user action such as taking medication, after the signals that the action has been completed, the selected programming is returned to the primary region. In instances where picture-in-picture is not enabled, the control component 30 can enable it to present the message within the primary or a secondary region.

In another instance, the user initiates the change in primary region through the communications port 24 and/or manual controls such as buttons, switches, knobs, etc. residing on the control device $16_2$.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A telemedicine system, comprising:
an audio-video switch that receives a plurality of different audio-video signals and conveys at least two of the different audio-video signals to an output device that concurrently displays a video portion of the at least two audio-video signals, each within a different display region of the output device, the audio-video switch including at least one of a wireless communications port for controlling the audio-video switch with a remote wireless device and control panel for manual control of the audio-video switch; and
a control device including one or more processors programmed to:
monitor a position of the audio-video switch,
power the audio-video switch through a bus connection with the audio-video switch,
monitor and control the audio-video switch through signals conveyed via the bus,
obtain at least one of a unique identification, a serial number, a software versions, and a firmware version of the audio-video switch via a universal serial port, and
automatically control the position of the audio-video switch to select which of the at least two different audio-video signals passed through the audio-video switch to the output device has its video portion displayed in each of the displays regions in response to a signal from a remote source, including (a) displaying a lower priority medical audio-video communication in the secondary display region and the user selected programming in the primary display region; (b) displaying a higher priority medical audio-video signal in a primary display region and user selected programming audio-video signal in a secondary display region; and (c) displaying a still higher priority medical audio-video signal on both the primary and secondary display regions when the audio-video signal is deemed critical.

2. The telemedicine system as set forth in claim 1, wherein the audio-video switch includes a processing component that combines at least two of the plurality of input audio-video signals, the two signals being combined by one of overlaying one of the signals over the other signal, the overlaid signals being passed to the output device to display both signals concurrently.

3. The telemedicine system as set forth in claim 1, wherein at least one of the plurality of different audio-video signals is associated with a tag that indicates the priority of the at least one signal relative to other audio-video signals and the priority is used to determine at least one of when and how to present the audio-video signal to the user.

4. The telemedicine system as set forth in claim 1, further including:
   a recording device connected with the audio-video switch, the control device causing the recording device to record audio/video signals and causing the recorded audio/video signals to be passed through the audio-video switch to the output device in accordance with instruction signals received from the remote source.

5. The telemedicine system as set forth in claim 4, wherein the recorded audio/video signals include lessons tailored to address a user's medical condition and are received over a low bandwidth connection and converted into high quality outputs.

6. The telemedicine system as set forth in claim 5, wherein the recorded audio/video signals are restored to full size prior to one of storing and playing the audio/video signal.

7. A telemedicine system including:
   an audio-video switch which (a) has a plurality of audio-video inputs including a first audio-video input configured for receiving entertainment audio-video signals and a second video input configured for receiving medical audio-video signals, (b) has audio-video outputs configured for connection to an audio/visual display device which has a picture-in-picture feature, and (c) has a router which selectively passes audio-video signals from the audio-video inputs to the audio-video output for display on the audio-video display device, the medical audio-video signals being received from a remote source and including:
      at least one of instructional programming directed to a patient corresponding to the audio visual switch and relating to a disease or physiological condition of the patient, reminders to take medicines, reminders of medical appointments, requests for the patient to monitor physiological conditions, motivational programming, requests for the patient to call a doctor's office, instructions for the patient associated with a scheduled medical procedure, test results, and real-time communications to the patient from medical personnel, and
      one of a plurality of control signals, the plurality including a higher priority control signal that indicates that the router is to display a user selected entertainment in the secondary display area and display the medical audio-visual signals in a primary area display and a lower priority control signal that indicates that the received medical audio-video signal should he displayed in the secondary display area and the user selected entertainment in the primary display area and further including:
   a control processor programmed to control the audio-video switch based on the received control signal, the control processor being connected with the router, the control processor being further programmed to:
      respond to the higher priority control signal to control the router to override user selected entertainment and supply the medical audio-visual signals to the primary display area and the user selected entertainment in the secondary display area,
      respond to the lower priority control signal to control the router to supply the user selected entertainment in the primary display area and the medical audio video signals to the secondary display area; and
      respond to a still higher priority control signal to control the router to supply the medical audio-visual signal on both the primary and secondary display areas when the medical audio-video signal is deemed critical.

8. The telemedicine system as set forth in claim 7, wherein at least one of the control processor and the audio-video switch validates parties attempting to communicate therewith and only authorized parties are allowed to communicate with the at least one of the control processor and the audio-video switch.

9. The telemedicine system as set forth in claim 7, wherein the control processor is further programmed to, when controlling the router to supply the medical audio-video signal to the audio-video output, record the entertainment audio-video signal and after supplying the medical audio-video signal to the audio-video output, automatically supplying the recorded entertainment audio-video signal to the audio-video output.

10. The telemedicine system as set forth in claim 7, wherein the control processor is programmed to validate the audio-video switch via at least one of a unique identification number, a serial number, a software version, and a firmware version of the audio-video switch.

11. The telemedicine system as set forth in claim 7, wherein the control processor is programmed to validate that the user is an authorized user.

12. The telemedicine system as set forth in claim 11, wherein in response to an unauthorized user trying to access the control processor, the control processor is configured to send information about the unauthorized user to a security or administrative authority.

13. The telemedicine system as set forth in claim 7, wherein when the medical audio-video signal is is a low bandwidth signal, the control processor is configured to record the low bandwidth medical audio-video signal and reconfigure the low bandwidth medical audio-visual signal into a high quality medical audio-visual signal for display on the audio-video display device.

14. The telemedicine system as set forth in claim 7, wherein the control processor and the audio-video switch are connected by a common bus by which the control processor at least controls and powers the audio-video switch.

15. The telemedicine system as set forth in claim 7, wherein the control processor is further programmed to before controlling the router to supply the medical audio-video signal to the audio-video output:
   validate the audio-video switch via at least one of a unique identification number, a serial number, a software version, and a firmware version of the audio-video switch;
   validate that the user is an authorized user.

16. A telemedicine method comprising:
   receiving a plurality of different audio-video signals with an audio-video switch, the audio-video signals including:
      entertainment audio-video signals and medical audio-video signals from a remote healthcare provider which convey at least one of instructional programming relating to a disease or physiological condition, reminders to take medicines, reminders of medical appointments, requests to monitor physiological conditions, motivational programming, requests to call a doctor's office, instructions associated with a scheduled medical procedure, test results, and real-time communications from medical personnel, and
      control commands which control the audio-video switch;

conveying a user-selected one of the received entertainment audio-video signals from the audio-video switch to a display device for display to the user;

with the audio-video switch in response to receiving a medical audio-video signal with a first priority control command, concurrently causing the medical audio-video signal to be displayed in a primary display area and the user selected entertainment audio-video signals to be displayed in a secondary display area;

with the audio-video switch, in response to receiving a medical audio-video signal with a second priority control command, causing the user selected entertainment audio-video signal to be displayed in the primary display area and the medical audio-video signal to be displayed in a secondary display area; and with the audio-video switch, in response to receiving a medical audio-video signal that is deemed critical, causing the medical audio-video signal to be displayed on both the primary and secondary display areas.

17. The method as set forth in claim 16, further comprising:

conveying electrical power to the audio-video switch via universal serial bus (USB) ports; and powering the audio-video switch with the conveyed electrical power.

18. The method as set forth in claim 16, further including:

conveying the control commands and electrical power to the audio-video switch over a common bus.

19. The method according to claim 16, further including:

with a control processor, validating the audio-video switch via at least one of a unique identification number, a serial number, a software version, and a firmware version of the audio-video switch.

20. The method as set forth in claim 19, further including:

with the control processor, validating whether the user is an authorized user and only permitting the audio-video switch to convey the medical audio-video signals to the display device for the authorized user.

21. The method as set forth in claim 20, further including:

in response to an unauthorized user trying to access the control device, sending information about the unauthorized user to a security or administrative authority.

\* \* \* \* \*